United States Patent [19]

Kobe et al.

[11] Patent Number: 4,701,526
[45] Date of Patent: Oct. 20, 1987

[54] PROCESS FOR PREPARING 9-(2-HYDROXYETHOXYMETHYL)-GUANINE, AND INTERMEDIATES USEFUL IN SAID PROCESS

[75] Inventors: Jŏze Kobe, Ljubljana; Jŏze Gnidovec; Pavle Zupet, both of Novo mesto, all of Yugoslavia

[73] Assignee: KRKA, tovarna zdravil, n.sol.o., Novo mesto, Yugoslavia

[21] Appl. No.: 807,724

[22] Filed: Dec. 11, 1985

[30] Foreign Application Priority Data

Dec. 22, 1984 [YU] Yugoslavia .................... 2190/84

[51] Int. Cl.⁴ .......................................... C07D 473/18
[52] U.S. Cl. .................................. 544/251; 544/276; 544/277
[58] Field of Search ............... 546/276; 544/277, 251; 514/257

[56] References Cited

U.S. PATENT DOCUMENTS 4,495,190  1/1985  Hagberg et al. .................... 544/277

Primary Examiner—Nicholas S. Rizzo
Attorney, Agent, or Firm—Pollock, Vande Sande & Priddy

[57] ABSTRACT

There is disclosed a process for preparing 9-(2-hydroxyethoxymethyl)-guanine (acyclovir) of the formula IV

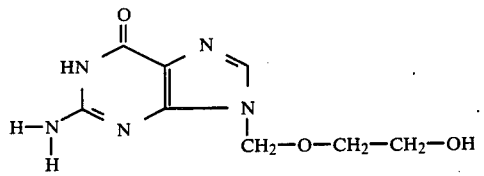

wherein a novel compound of the formula I

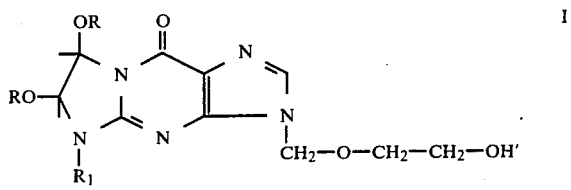

wherein R and R' may be the same or different and represent hydrogen, $(C_1-C_8)$acyl or benzyl and $R_1$ represents $(C_1-C_8)$acyl, is hydrolyzed under mild basic conditions. Also disclosed is the novel compound of the formula I, a process for the preparation thereof by condensing a novel compound of the formula II

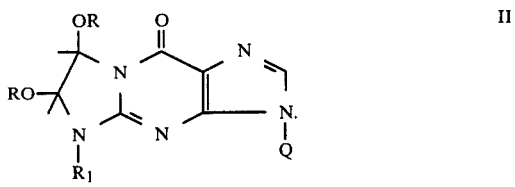

with a compound $A-CH_2-O-CH_2CH_2-OR'$ (A is a leaving group, Q is hydrogen or a leaving group), the novel compound of the formula II and a process for the preparation thereof by means of condensing glyoxal hydrate and a compound of the formula V

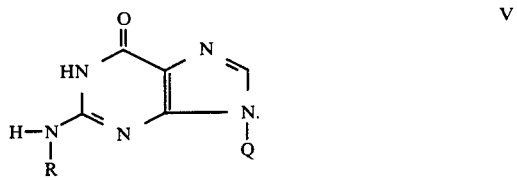

14 Claims, No Drawings

PROCESS FOR PREPARING 9-(2-HYDROXYETHOXYMETHYL)-GUANINE, AND INTERMEDIATES USEFUL IN SAID PROCESS

The present invention relates to a process for preparing 9-(2-hydroxyethoxymethyl)-guanine (acyclovir) of the formula IV

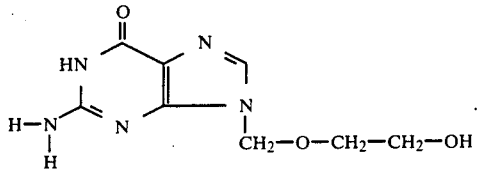

via novel $N^2$,1-substituted purins of the general formula

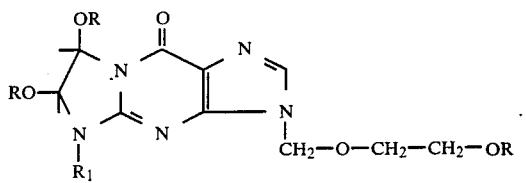

wherein R and R' may be the same or different and represent hydrogen, $(C_1-C_8)$acyl or benzyl and $R_1$ represents $(C_1-C_8)$acyl, to these novel intermediates of the formula I, to process for preparing intermediates of the formula I, to novel intermediates of the formula II hereinafter and to a process for the preparation thereof.

Acyclovir is a well-known agent for therapy of virus infections (Zovirax) (Schafer H. J., Beauchamp L. M., de Miranda P., Elion G. B. Bauer D. J., and Collins P. (1978) Nature (London) 272 583-585).

R is preferably acetyl group and isobutyryl group and $R_1$ as preferably acetyl group.

The compound of the formula IV is prepared according to the inventive process in such a way that a compound of the general formula I

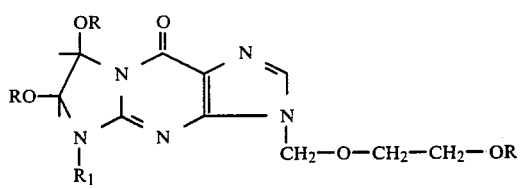

is converted, i.e. hydrolyzed, into the compound IV under mild basic conditions, preferably in 50% aqueous methyl amine at room temperature or under slight heating.

The compounds of formula I are novel compounds and represent another object of the invention.

They are prepared by a process, which is also an object of the present invention, in such a way that a compound of the general formula II

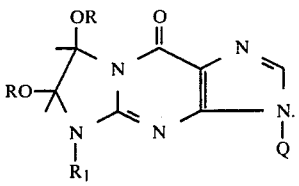

is condensed with a compound of the formula III

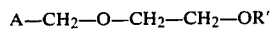

$$A-CH_2-O-CH_2-CH_2-OR'$$

wherein A represents a leaving group and Q represents a hydrogen atom or a leaving group, whereas R, R' and $R_1$ have the above meanings.

The leaving group A may be e.g. acetoxy or halo group and the leaving group Q may be, e.g., acetyl.

As reaction mediums toluene and related aromatic solvents or dichloromethane and related halogenated hydrocarbons are used. The process may be carried out at 110° C. in toluene with $A=CH_3COO$ as leaving group and at room temperature with $A=$halo group in dichloroethane, resp. As catalysts e.g. p-toluenesulfonic acid, $AlCl_3$, $SnCl_4$, $HgBr_2$ are used.

The compounds of the formula II are novel compounds and represent a further object of the invention. The process for the preparation thereof is also a novel process.

Thus, a further object of the invention is a process for preparing compounds of the general formula II, which is characterized in that a $N^2$-substituted guanine derivative of the formula V

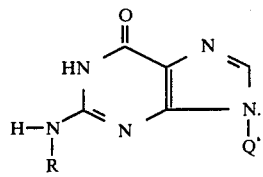

is condensed with glyoxal hydrate into a compound of the formula II

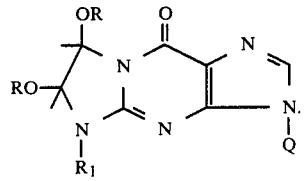

wherein R, Q and $R_1$ have the above-defined meanings.

The compound of the formula II is thus prepared from $N^2$,9-diacetylguanine (Hrebanecky H., Farkas J. in: NUCLEIC ACID CHEMISTRY, Part I, p. 13; L. B. Townsend, R. Stuart Tipson Ed.) and glyoxal monohydrate in dry pyridine at room temperature. The reaction is usually carried out in the ratio 3.5-8.0 mole glyoxal per 1 mole $N^2$,9-diacetylguanine. The obtained intermediate II (R=H) is further acrylated with an appropriate anhydride in pyridine to intermediate II (R is preferably acetyl or isobutyryl) and the latter is condensed with the compound of the formula III (A is preferably $-CH_3COO$) in toluene at reflux temperature and in the presence of catalytic amounts of an acid (preferably p-toluenesulfonic acid). The reaction is generally carried out with an excess of the reactant III (1.2 mole) over the compound II (1 mole).

The starting compounds for preparing novel compounds according to the invention are disclosed in patent as well as in scientific literature. By preparing compounds of the formula I according to the present invention, there have increased the solubility and the reactivity of the starting raw material for the preparation of acyclovir ($N^2$,9-ciacetyl-guanine) in aromatic solvents and especially in halogenated aliphatic solvents. The selectivity for condensation with the compounds of the general formula II has increased, too, preferably in the 9-position, whereby the total reaction yields have increased.

The processes are illustrated by the following non-limiting Examples.

EXAMPLE 1

$N^2$,9(7)-diacetyl guanine

Guanine (152 g) is suspended in N-methyl-2-pyrrolidone (800 ml) and acetic anhydride (250 ml). The reaction mixture is heated to 150° C. and stirred for 2 to 3 hours so that all guanine is dissolved. The solution is cooled to room temperature and left in refrigerator overnight. Crystals are sucked off, suspended in ethyl acetate (500 ml), repeatedly sucked off and washed with fresh ethyl acetate (50 ml). The product is dried in a drier at 50° C. to a constant weight. The yield is 200 g of $N^2$-9(7)-diacetyl guanine (85%). The reaction mixture liquor is returned to the reaction vessel, guanine (100 g) and acetic anhydride (150 ml) are added thereto and the process is repeated. There are obtained further 150 g of $N^2$,9(7)-diacetyl guanine. The total yield is 96%.

EXAMPLE 2

Glyoxal-$N^2$-acetyl guanine adduct

Glyoxal monohydrate (280 g) is suspended in dry pyridine (950 ml) and the reaction mixture is stirred for 1 hour at 50° C., whereby all glyoxal is dissolved. To this solution $N^2$,9(7)-diacetyl guanine (236 g) is added and the reaction mixture is stirred vigorously for 1.5 hours. Pyridine is evaporated at 50° C. and reduced pressure (67 mbar); water (1000 ml) is added to the residue and the stirring is continued for half an hour, whereat the solid residue is dissolved. The azeotrope (pyridine-water) (400 ml) is distilled off at 50° C. under reduced pressure. A white precipitate begins to form already during evaporation. The residue in the flask is poured into cold water (2500 ml), stirred for about 1 hour and left in a refrigerator overnight. The precipitate is sucked off, washed with water (150 ml) and dried in a drier. Yield: 227 g of the adduct of the formula II (R=hydrogen, $R_1$=CH$_3$CO) (90%), m.p. 223° C.

Analysis for $C_9H_9N_5O_4$; m/e=251.

$^1$H NMR-DMSO-d$_6$ $\delta_{DSS}$: 2.68 (s, 3, CH$_3$CO); 5.55 (dd, 2, CH); 8.10 (s, 1, H$_8$).

EXAMPLE 3

Tetraacetyl-glyoxal-guanine adduct

Adduct II (252 g) (R=H) is dissolved in pyridine (2500 ml). Acetic anhydride (280 ml) is poured into the solution and the stirring is continued for 1.5 hours at room temperature. Pyridine is evaporated at 50° C. under reduced pressure. Ethyl acetate (1000 ml) is poured to the residue, the mixture is stirred for 1 hour at room temperature and left in a refrigerator overnight. White crystals are sucked off, washed with ethyl acetate (150 ml) and dried in a drier to a constant weight. There are obtained 272 g of product II (R=CH$_3$CO, Q=CH$_3$CO) (72%). Ethyl acetate is washed three times with a 5% NaHCO$_3$ solution and finally with water, dried with Na$_2$SO$_4$ and at evaporation to dryness, there are obtained additional 72 g of the product. The total yield is 93%, m.p. 197°–199° C. from ethyl acetate.

Analysis for $C_{15}H_{15}N_5O_7$; m/e=377.

$^1$H NMR CDCl$_3$ $\delta_{TMS}$: 2.1 (ds, 6 Ac), 2.7 (s, 3, NAc); 2.83 (s, 3, NAc); 6.8 (broad, 2, CH); 8.35 (s, 1 H$_8$)

EXAMPLE 4

Diacetoxy-glyoxal-$N^2$-acetylguanine adduct

Method A

Adduct II (252 g) (R=H, Q=H) is dissolved in pyridine (2500 ml) and acetic anhydride (280 ml). The mixture is stirred for 1.5 hours at room temperature, pyridine is evaporated at 50° C. under reduced pressure; to the residue there is added 50% ethyl alcohol (80 ml) and the mixture is heated to reflux temperature. Heating at reflux is continued for 15 minutes until a clear solution is obtained, the contents of the flask are slowly cooled to room temperature and left in a refrigerator overnight. The precipitated crystals are sucked off, washed with 50% ethyl alcohol and dried in a drier. Yield: 234 g (70%), m.p. 242°–243° C.

Analysis for $C_{13}H_{13}N_5O_6$; m/e=335.

$^1$H NMR CDCl$_3$ $\delta_{TMS}$: 2.15 (s, 6, Ac); 2.83 (s, 3, NAc); 6.82; 6.93 (dd, 2, CH); 8.15 (s, 1, H$_8$).

Method B

Compound II (272 g) (R=Ac, Q=Ac) is suspended in 50% ethyl alcohol (1200 ml), the suspension is heated at reflux for 15 minutes or for such a period that all solid is dissolved. The contents are slowly cooled to room temperature and put into a refrigerator overnight. Crystals are sucked off, washed with 50% ethyl alcohol and dried. There are obtained 173 g (72%) of the product II (R=Ac, Q=H).

EXAMPLE 5

Method A 9-(2-acetoxyethoxymethyl)-diacetoxy-glyoxal-$N^2$-acetyl guanine adduct (R=CH$_3$CO, $R_1$=CH$_3$CO)

Compound II (3.35 g) (R=CH$_3$CO, $R_1$=CH$_3$CO, Q=H) and 2-oxo-1,4-butan-dioldiacetat III (2 g; R=CH$_3$CO) (Senkus M., J. Amer. Chem. Soc. 68 734 (1946)) in dry toluene (40 ml) are stirred for 7 hours at reflux. Toluene is evaporated to dryness, benzene (150 ml) is added, the suspension is heated to ebullition under stirring and is hot filtered over a glass filter. On the filter there remain 2 g (44%) of compound I (R=CH$_3$CO, $R_1$=CH$_3$CO), which is crystallized from toluene, m.p. 97°–99° C.

Analysis for $C_{16}H_{20}N_5O_9$; m/e=457.

$^1$H NMR CDCl$_3$ $\delta_{TMS}$: 2.05 (s, 3, Ac); 2.12 (s, 3, Ac); 2.35 (s, 3, Ac); 2.75 (s, 3, NAc); 3.69 (m, 2, CH$_2$O); 3.74 (m, 2, CH$_2$O); 5.5 (s, 2, NCH$_2$); 6.87 (dd, 2, CH); 7.84 (s, 1, H$_8$).

EXAMPLE 6

Method B

Diisobutyroxy-glyoxal-$N^2$-acetyl guanine adduct II
(R=—COCH(CH$_3$)$_2$, R$_1$=CH$_3$CO, Q=H)

Compound II (1.26 g) (R=H, R$_1$=CH$_3$CO, Q=H) is suspended in dry pyridine (25 ml), isobutyric anhydride (2.5 ml) is added and the mixture is stirred overnight. Pyridine is evaporated, the residue is dissolved in ethyl acetate (40 ml) and the solution is washed with water (40 ml), a 5% NaHCO$_3$ solution (3×20 ml) and finally with water (20 ml). The solution is dried over Na$_2$SO$_4$ and there are obtained 1.55 g of a crude product. 50% ethyl alcohol (50 ml) is added and it is heated at reflux for 15 minutes. The solution is evaporated and there is added a small amount of ethyl acetate. There are obtained 1.2 g of the product with m.p. 171°-172° C.

Analysis for C$_{17}$H$_{21}$N$_5$O$_6$; m/e=391.

$^1$H NMR CDCl$_3$ $\delta_{TMS}$: 1.16 (s, 3, CH(CH$_3$)$_2$); 1.25 (s, 3, CH(CH$_3$)$_2$); 2.53 (m, 2, CH(CH$_3$)$_2$); 2.8 (s, 3, NAc); 6.7 (dd, 2, CH); 8.15 (s, 1, H$_8$).

EXAMPLE 7

9-(2-acetoxyethoxymethyl)-diisobutyroxyglyoxal-$N^2$-acetylguanine adduct

Compound II (200 mg) (R=COCH(CH$_3$)$_2$, R$_1$=CH$_3$CO, Q=H, R'=CH$_3$CO) is heated at reflux for 5 minutes in hexamethyldisilazane in the presence of a catalytic amount of ammonium sulfate. Within said period all starting material is dissolved and there is obtained a silylated product II (R=COCH(CH$_3$)$_2$, R$_1$=CH$_3$CO, Q=Si(CH$_3$)$_3$), which is, immediately after evaporating the excess of the solvent, dissolved in dry benzene (15 ml) and there are added HgBr$_2$ (180 mg) and BrCH$_2$OCH$_2$CH$_2$OAc (100 mg) Robins M. J., Hatfield P. W., Canad. J. Chem. (1981) 60 547–553). The mixture is heated at reflux overnight, the solvent is evaporated and the residue is dissolved in chloroform. The solution is washed with a 20% KJ solution (2×10 ml) and water (2×10 ml), dried over Na$_2$SO$_4$ and evaporated to foam. Yield: 210 mg of the crude product. After chromatography on 10 g of silicagel, there is obtained the compound I (R=—COCH(CH$_3$)$_2$, R$_1$=CH$_3$CO, R'=CH$_3$CO) (120 g).

$^1$H NMR CDCl$_3$ $\delta_{TMS}$: 1.11 (s, 6, CH(CH$_3$)$_2$); 1.25 (s, 6, CH(CH$_3$)$_2$; 2.06 (s, 3, Ac); 2.8 (s, 3, NAc); 3.7 (m, 2, OCH$_2$); 3.76 (m, 2, OCH$_2$); 5.5 (s, 2, NCH$_2$O); 6.85 (dd, 2, CH); 7.80 (s, 1 H$_8$).

EXAMPLE 8

9-(2-hydroxyethoxymethyl)-guanine (acyclovir)

Compound I (1 g) (R=CH$_3$CO, R$_1$=CH$_3$CO) is put into 50% methaylamine (10 ml). The reaction mixture is cleared at once in exothermic reaction, heated for further 15 minutes on a steam bath or left overnight at room temperature. The solvent and excessive amine are evaporated under reduced pressure, ethyl alcohol (10 ml is added and the solvent is evaporated once more. Methyl alcohol (15 ml) is added to the residue, methyl alcohol is decanted and the residue is crystallized from a methyl alcohol/water mixture to obtain product IV (400 mg; 81%), m.p. 264°-266° C. m/e 225.

$^1$H NMR DMSOd$_6$ $\delta_{DSS}$: 3.49 (m, 4, OCH$_2$); 4.69 (s, 1, OH); 5.4 (s, 2, NCH$_2$O); 6.54 (s, 2, NH$_2$); 7.84 (s, 1, H$_8$).

We claim:

1. Process for preparing 9-(2-hydroxyethoxymethyl)-guanine of the formula

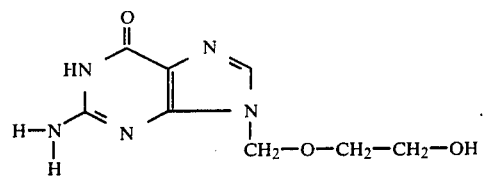

characterized in that a compound of the formula I

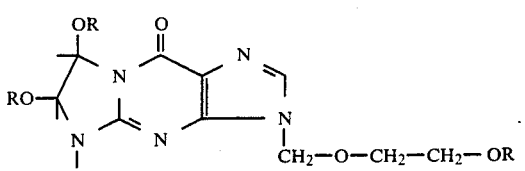

wherein R and R' may be the same or different and represent hydrogen, (C$_1$-C$_8$)acyl or benzyl and R$_1$ represents (C$_1$-C$_8$)acyl is hydrolyzed under mild basic conditions.

2. A compound of the formula I

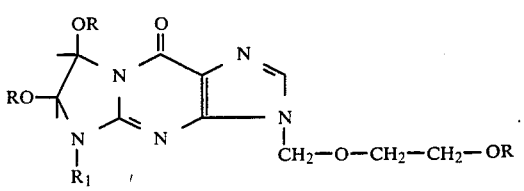

wherein R and R' may be the same or different and represent hydrogen, (C$_1$-C$_8$)acyl or benzyl and R$_1$ represents (C$_1$-C$_8$)acyl.

3. A compound of the formula II

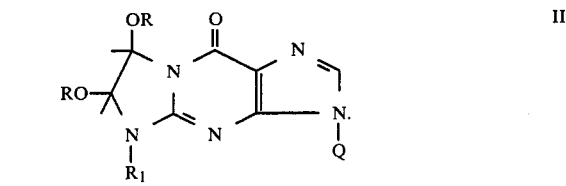

wherein R represents hydrogen, (C$_1$-C$_8$)acyl or benzyl, Q represents a hydrogen atom or a leaving group, and R$_1$ represents (C$_1$-C$_8$)acyl.

4. The compound of claim 2 wherein R is acetyl or isobutyryl.

5. The compound of claim 4 wherein R$_1$ is acetyl.

6. The compound of claim 2 wherein R$_1$ is acetyl.

7. The compound of claim 3 wherein R is acetyl or isobutyryl.

8. The compound of claim 7 wherein R$_1$ is acetyl.

9. The compound of claim 3 wherein R$_1$ is acetyl.

10. The compound of claim 2 wherein R is acetyl and R$_1$ is acetyl.

11. The compound of claim 3 wherein R is acetyl and R$_1$ is acetyl.

12. The compound of claim 3 wherein Q is acetyl.

13. The compound of claim 3 wherein R is acetyl, R$_1$ is acetyl, and Q is acetyl.

14. The compound of claim 10 wherein R$_1$ is acetyl.

* * * * *